United States Patent [19]
Discko, Jr. et al.

[11] Patent Number: 5,150,495
[45] Date of Patent: Sep. 29, 1992

[54] DISPOSABLE DENTAL BRUSH

[75] Inventors: John Discko, Jr., Hamden; William B. Dragan, Easton, both of Conn.

[73] Assignee: Centrix, Inc., Shelton, Conn.

[21] Appl. No.: 671,523

[22] Filed: Mar. 19, 1991

Related U.S. Application Data

[63] Continuation-in-part of Ser. No. 325,888, Mar. 20, 1989, Pat. No. 5,001,803.

[51] Int. Cl.⁵ .......................... A46B 9/04; A46B 17/02
[52] U.S. Cl. ..................................... 15/167.1; 15/106; 15/160; 15/172; 15/176.1; 15/176.6
[58] Field of Search ................. 15/160, 166, 167.1, 15/172, 144 R, 169, 184, 159 R, 176.1, 176.2, 176.3, 176.6, 106; 132/321

[56] References Cited

U.S. PATENT DOCUMENTS

3,106,738 10/1963 Bohne ................................... 15/184
3,609,789 10/1971 Slater ................................ 15/172 X
4,712,266 12/1987 Yamaki ............................. 15/167.1
4,731,896 3/1988 de La Tour ........................... 15/106
4,805,646 2/1989 Shimenkov ..................... 132/321 X Primary Examiner—Edward L. Roberts
Attorney, Agent, or Firm—Arthur T. Fattibene; Paul A. Fattibene

[57] ABSTRACT

A disposable dental brush for applying various dental materials onto a tooth in thin even, coatings, e.g. etchants, sealants, bonding agents, tints, opaquers, varnishes and the like that includes an elongated straight handle having a tuft of bristles connected to one end thereof. The elongated handle is constructed so as to allow the portion thereof adjacent to the brush end to be readily bent so as to angularly dispose the brush end relative to the longitudinal axis of the handle. The arrangement is such that the brush can be used either as a straight brush or an angularly bent brush to reach difficult areas of the mouth or teeth. Also, the brush is made of inexpensive plastic material so as to render it readily expendable or disposable after each use.

4 Claims, 7 Drawing Sheets

DISPOSABLE DENTAL BRUSH

RELATED APPLICATIONS

This application is a continuation-in-part application of our co-pending application Ser. No. 07/325,888 filed Mar. 20, 1989, now U.S. Pat. No. 5,001,803.

FIELD OF INVENTION

This invention is directed to dental brushes for applying various dental materials to a tooth structure in thin, uniform coatings.

PROBLEM AND PRIOR ART

Various types of paint brushes are readily known. Included in the known paint brushes are artist brushes which comprise an elongated handle having a plurality of bristles or brush hairs connected to one end. The known paint brushes are generally not intended to be rendered readily disposable. As a consequence, such brushes are required to be cleaned and maintained between uses.

Heretofore, such brushes have been minutized for use in dentistry as many dental procedures require various dental materials, such as sealants, bonding agents and the like, to be painted onto a tooth in thin, even coatings or layers. However, because of the need for sterilization to prevent cross-contamination between patients, the use of miniature paint brushes required frequent cleaning. Because the dental materials in current use include various materials that cure in a relatively short period, cleaning and/or sterilization of such brushes was frequently impossible. With the advent of AIDS, contagious hepatitis and other communicable diseases and the quick setting dental materials, a disposable brush is desirable.

A known disposable dental type brush comprised a reusable handle portion that included a fixed angular end portion to which a disposable tuft of bristles was detachably connected. While the bristles or tuft of bristles was rendered readily disposable after each use, the handle, being a reusable component, had to be sterilized between patients to ensure against cross-contamination. Such known reusable brush construction with detachable bristles is relatively expensive. Also, it invariably happens that after several uses, the dental materials would tend to accumulate onto the reusable handle portion to result in a time-consuming cleaning problem. Such known reusable brush handles had another noted disadvantage in that they were not well suited for use on anterior teeth, due to the fixed angular offset of the brush end. Thus, while the angular offset, reusable handle with disposable brush heads solved some of the problems with which a dentist is confronted, it did not solve all of the problems involved in painting dental materials onto a tooth structure, as the reusable handle still required cleaning and sterilization between patients. Also, the fixed angular offset brush end rendered the use thereof inconvenient when working in certain areas of the mouth.

Another disadvantage noted with the dental brushes having a reusable handle was that the disposable brush tips often did not fit well to the end of the handle and caused such brush tips to fall out if too loose, or difficult to insert if too tight, as it was difficult to maintain the tolerances of the disposable brush ends.

Another reusable dentist brush, such as manufactured by or for L. D. Caulk, a division of Dentsply International, consisted of an artist type brush in which the brush tufts were held in place onto the end of a handle by a crimped metal collar. The metal collar was prebent to a fixed angle. Such brushes are relatively expensive and were intended to be cleaned after each use and re-used. To facilitate the cleaning thereof, the manufacturer would include a bottle of solvent for cleaning such brushes. Also, the pre-fixed angle brush was limited to the extent it was not convenient for use on anterior teeth for which a straight brush was more appropriate. Also, the fixed angle was not optimal for all hard to reach areas of the mouth.

OBJECTS

An object of this invention is to provide a readily inexpensive dental brush that is rendered totally disposable after each use.

Another object of this invention is to provide a dental brush having a bendable end portion whereby the brush end can be optionally disposed and maintained in variously fixed angular relationships relative to the longitudinal axis of the brush handle.

Another object of this invention is to provide a dental brush that is relatively simple in construction, positive in operation and inexpensive to manufacture.

Another object is to provide a dental brush wherein the brush end can be readily adjusted by the dentist to enable the dentist to work in all areas of the mouth with the optimum ease and convenience.

Another object is to provide a dental brush having a flexible or bendable brush end that is integrally constructed as a unitary unit.

SUMMARY OF THE INVENTION

The foregoing objects and other features and advantages are obtained by a dental brush having a generally elongated handle portion preferably made of an inexpensive material, e.g., a suitable plastic, whereby the entire brush can be rendered readily expendable after each use. Connected to one end of the brush is the brush tip which generally comprises a tuft of bristles suitably secured to one end of the handle portion. In accordance with this invention, the handle portion is provided with a flexible or hinge construction located adjacent the brush end, whereby the brush end can be optionally bent so that the brush end can be bent or flexed between an axially aligned position relative to the longitudinal axis of the handle portion to various predetermined offset angular positions relative to the longitudinal axis of the handle portion so as to facilitate access to hard to reach areas. The flexed or bent portion of the handle is constructed so that the angular offset is maintained in the adjusted bent position. In one form of the invention, the flexing or bendable portion is integrally formed of the same material used for making the brush handle portion and functions as a living hinge. In another form of the invention, the flexible or bendable portion may be formed by a wire connected to the handle portion. In another form of the invention, the handle portion may be provided with a plurality of bendable portions intermediate the ends thereof to enable the brush end to be offset or angularly disposed in a compound angular relationship.

FEATURES

A feature of this invention resides in the provision of a totally expendable dental brush whereby the brush end can be optionally disposed between an axial aligned position to a variety of predetermined angularly offset positions relative to the longitudinal axis of the handle portion.

Another feature resides in the provision wherein the flexible portion of the brush is integrally formed as a portion of the handle portion.

Another feature of this invention is to provide the handle portion of the brush with more than one bendable or flexible portion whereby the brush end can be disposed at a compound angle relative to the longitudinal axis of the brush.

Other features and advantages will become readily apparent when considered in view of the drawings and detailed description thereof, wherein.

DETAIL DESCRIPTION

Referring to the drawings, there are illustrated various embodiments of a disposable dental brush embodying the invention. In dentistry, there are a host of procedures that require a dentist to paint onto the tooth structure of a patient various dental materials such as sealants, bonding agents, tints, opaquers, varnishes and other liquid type materials in thin, even coatings or layers. Such procedures are of particular importance in cosmetic dentistry and in preventive dentistry, e.g. placing sealants on children's teeth. To avoid tedious problems of cleaning such brushes and to minimize cross-contamination of patients, the present invention is directed to a totally disposable dental brush that is rendered readily expendable after each use.

Figure 1:
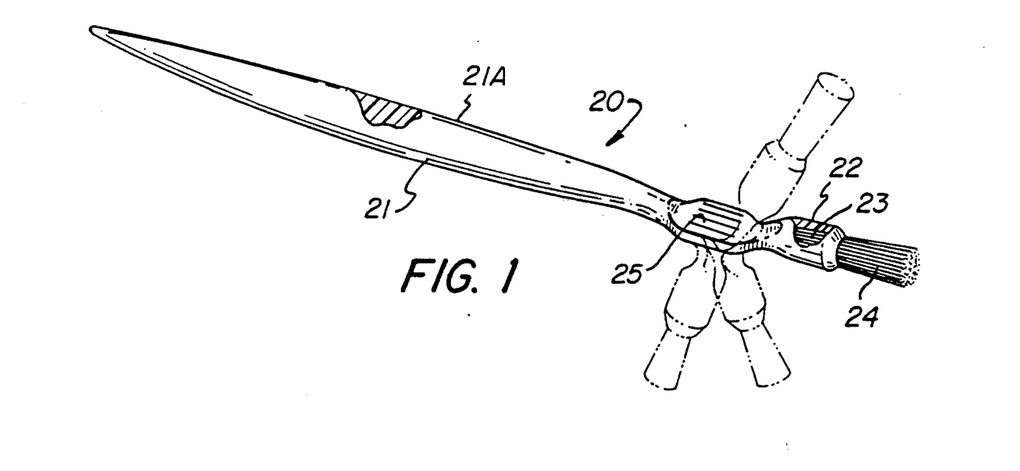
FIG. 1 is a perspective view of a disposable dental brush embodying the invention.

Referring to the drawing, there is shown in FIG. 1, one of the preferred forms of the invention. As shown, the disposable dental brush 20 of FIG. 1 comprises a handle portion 21 which is formed of a suitable inexpensive material, e.g. a suitable plastic that can be readily molded as an integral unit. The illustrated brush handle 21 comprises an elongated handle portion which is shaped intermediate the ends thereof with a thickened portion as indicated at 21A, which tapers inwardly toward the opposed ends thereof, so as to provide a gripping portion to give the dentist a comfortable and controllable grip on the brush. The brush end 22 of the handle portion is provided with a bore 23 to provide a seat for receiving a tuft of bristles 24. The tuft of bristles are fixedly secure within the seat defined by bore 23, e.g. by a staple or adhesive or by another other suitable means.

In accordance with this invention, the handle portion adjacent the brush end 22 is provided with a hinging means whereby the brush end can be readily bent relative to the longitudinal axis of the handle portion 21. As shown in FIG. 1, the hinging means comprises a flattened hinge section 25 which defines a reduced section between the handle portion 21A and the brush end 22 which is integrally formed of the material from which the handle portion is formed. The reduced or flattened section 25 is sufficiently rigid so as to maintain the brush end 22 co-axially disposed relative to the longitudinal axis of the handle portion, so that the brush 20 may be used by the dentist as a straight brush when working on anterior teeth. The reduced or bendable portion 25 is also sufficiently flexible so as to permit the dentist to angularly offset the brush end 22 relative to the longitudinal axis of the handle portion 21 as shown in the various dotted line positions. The arrangement is such that the dentist or user can bend the brush end to any predetermined angular position that may be necessary to reach difficult areas of the mouth, e.g. the most rear posterior teeth. Also, the arrangement is such that the material from which the brush is formed will maintain the adjusted position of the brush end 22. Thus, the flexible portion 25 functions as a hinge between the gripping portion 21A of the handle and the brush end 22 of the brush and will securely retain the brush end in the adjusted position thereof. With a single brush as described, a dentist can reach all areas of the mouth in a simple and convenient manner, and which brush will enable the dentist to coat in even layers any tooth with ease and comfort for both dentist and patient. After use, the entire brush is disposed of, thus eliminating completely the need for any clean up and/or sterilization to guard against cross-contamination between patients, which has been an age-old problem in dentistry.

Figures 2, 3:
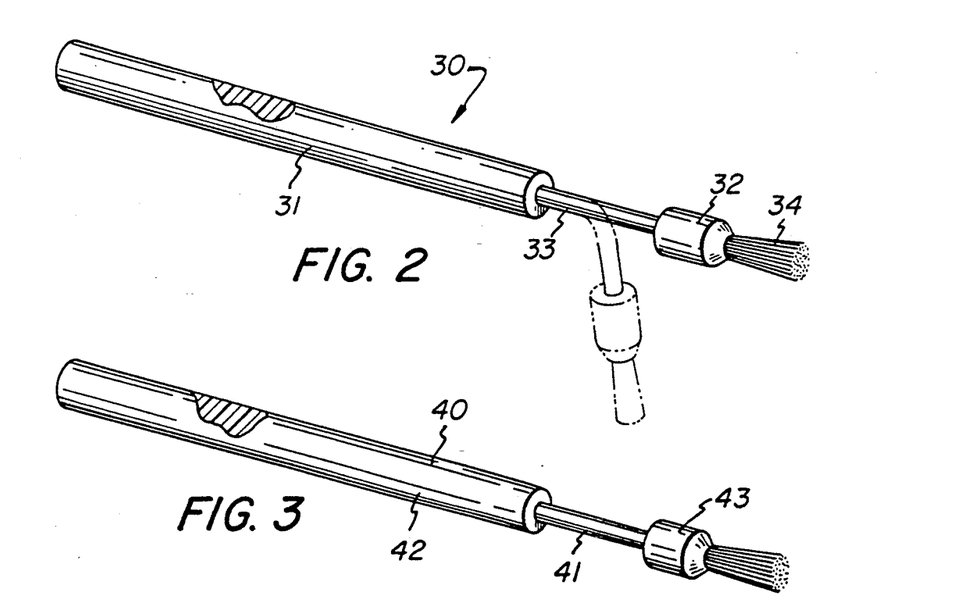
FIG. 2 is a modified embodiment of the invention.
FIG. 3 comprises still another modified embodiment of the invention.

FIG. 2 illustrates another modification of the invention. In this form of the invention, the dental brush 30 comprises a handle portion 31 connected to the brush end 32 by a reduced section 33 having a rod like configuration or circular cross-section. The tuft of bristles 34 is secured to the brush end 32 in a manner hereinbefore described. In this form of the invention, the reduced section 33 is integrally formed with the handle portion 31 and brush end 34 and made of the same material. The reduced portion 33 is rendered sufficiently flexible for angularly disposing the brush end 32 relative to the longitudinal axis of the handle portion 31. In this form of the invention, it will be noted that the brush end 32 can be bent at any angle within a 360 degree radius about the longitudinal axis of the brush handle 31. As described with respect to FIG. 1, the nature of the material of the reduced or hinge section 33 is such that it will maintain the brush end 32 in the adjusted position. Also, the brush 30 can be readily used by the dentist as a straight brush or as an angularly disposed brush, thereby allowing the dentist the flexibility to reach all areas of the mouth. It too is rendered readily disposable after use.

FIG. 3 illustrates an embodiment similar to that of FIG. 2, except that the brush 40 has a reduced hinge section 41 which comprises a length of wire-like material which may be made of a flexible metal or rod. In this form, the rod 41 is fixedly connected to and between the handle portion 42 and the brush end 43 by suitable means. In all other respects, the construction and operation is similar to that herein described with respect to FIG. 2.

Figure 4:
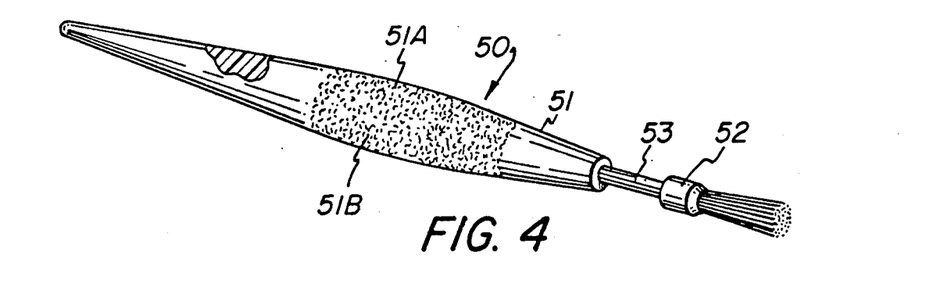
FIG. 4 is another modified embodiment of the invention.

FIG. 4 illustrates a brush construction 50 in which the handle portion 51 is formed with a bulging center portion as indicated at 51A that tapers inwardly toward the opposed ends thereof. The intermediate portion of the handle portion 51 is provided with a slightly roughened surface 51B to facilitate the gripping thereof. The hinge means 53 between the handle portion 51 and the brush end portion 52 may be formed as described in either FIGS. 2 or 3. In all other respects, the brush 50 is similar to that hereinbefore described.

Figures 5, 6, 7, 8, 9, 10:
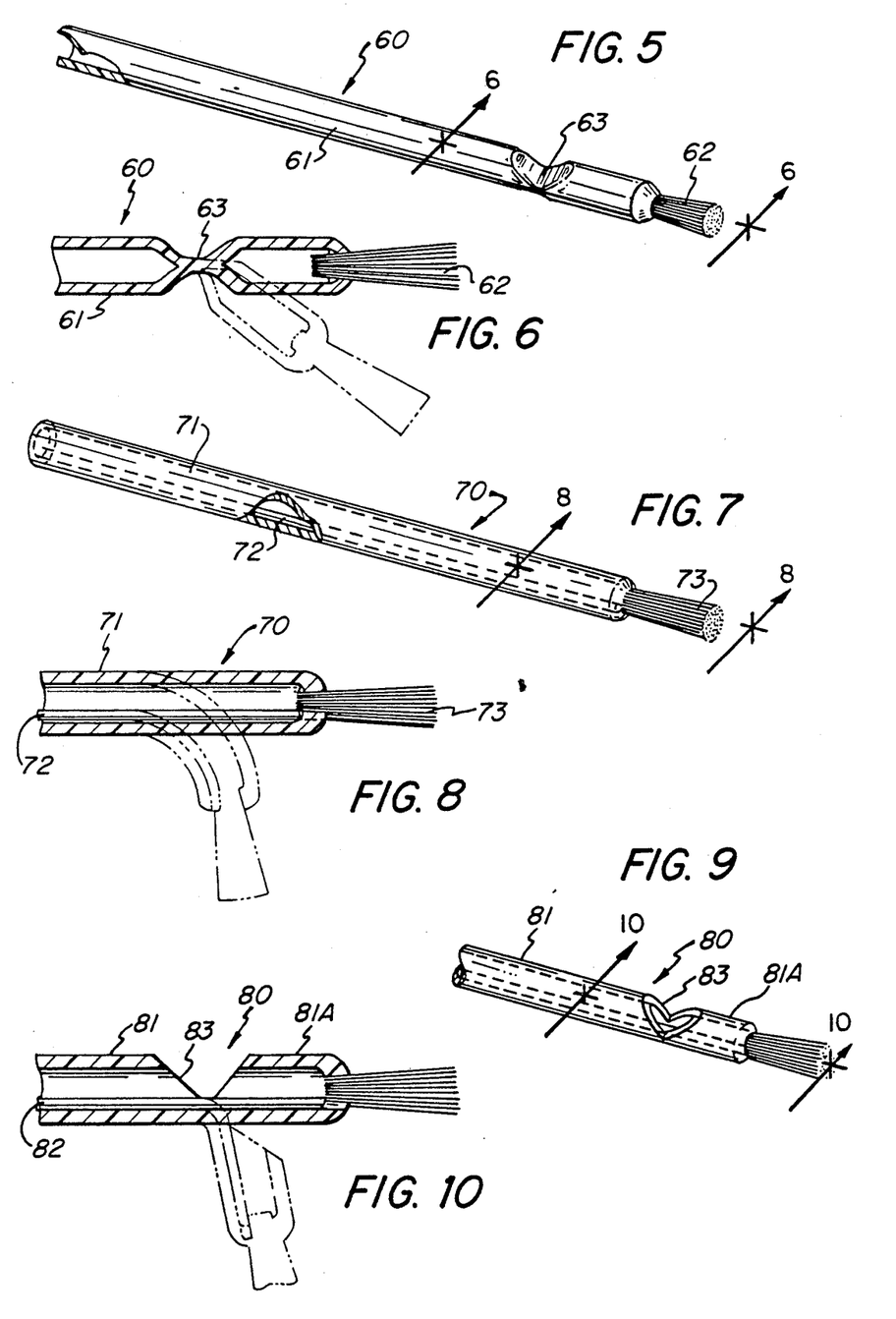
FIG. 5 is another modified embodiment.
FIG. 6 is a fragmentary sectional view taken along line 6—6 on FIG. 5.
FIG. 7 is a perspective view of another modified embodiment having a portion broken away.
FIG. 8 is a section view taken along line 8—8 on FIG. 7.
FIG. 9 is a fragmentary perspective view of another modification.
FIG. 10 is a section view taken along line 10—10 on FIG. 9.

FIGS. 5 and 6 illustrate still another modification embodying the invention. As shown in FIGS. 5 and 6, the brush 60 includes a handle portion 61, which is formed of a tubular disposable plastic material of a predetermined length. In this form of the invention, a tuft of bristles 62 is suitable inserted into and secured in one end of the tubular handle portion 61. Intermediate the handle portion and adjacent to the brush end 62, the handle portion is compressed to define a flexible hinge section 63. Thus, as shown in FIG. 6, the brush end can be readily flexed and angularly disposed relative to the longitudinal axis of the brush 60 in a manner hereinbefore described. In this form, the hinge section 63 is sufficiently rigid to permit the dentist to use the brush as a straight brush as shown in FIG. 5 or as a bent brush as shown in FIG. 6.

FIGS. 7 and 8 illustrate another modified form of the invention. In this form of the invention, the brush 70 is provided with a brush handle 71 which may be made of a material which may not have a memory or the ability to maintain a bent or angular position, e.g. tubular paper or other inexpensive material incapable of maintaining a bent position. In this arrangement, a length of bendable wire 72 extends longitudinally along the length of the handle portion 71, and is suitably secured thereto. In the construction described, the brush end can be bent relative to the longitudinal axis of the brush and maintained in the angular adjusted position by the flexibility of the wire 72. It will be understood that the tuft of bristles 73 is inserted and secured to the end of the handle portion 71 in a manner similar to that hereinbefore described. Thus, the construction of FIGS. 7 and 8 also allows a dentist to use the brush 70 as either a straight brush or a bent brush that is also readily expendable after each use thereof.

FIGS. 9 and 10 illustrate a slightly modified variation of the embodiment disclosed and described with respect to FIGS. 7 and 8. In this form of the invention, the handle portion 81 of brush 80 is also formed of a tubular handle portion having a length of flexible wire 82 extending therealong as described in FIGS. 7 and 8. However, to facilitate the flexing or bending of the brush end portion 81A, the handle portion is provided with a notched out area 83 in the area about which the brush end is adapted to be bent. In this form of the invention, the brush end 81A can be variably flexed in one direction through approximately 180 degrees and in the opposite direction a limited amount depending upon the notched out area. In all other respects, the construction of FIGS. 9 and 10 is similar to that hereinbefore described.

Figure 11:
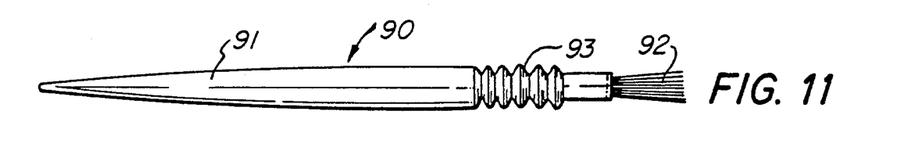
FIG. 11 illustrates another modified form of the invention wherein the hinging portion is defined by pleated folds.

FIG. 11 illustrates yet another modification of a disposable bendable type dental brush 90. In this form of the invention, the brush handle 91 is formed of a suitable plastic material having a tuft of bristles 92 defining the brush end suitably secured in one end thereof. The bendable portion comprises a pleated section 93 to define a plurality of accordion-like folds. The pleated section 93 is sufficiently rigid so that the brush 90 can be used as straight brush, and which pleated section is sufficiently flexible so as to allow a dentist to angularly dispose the brush end relative to the longitudinal axis of the brush handle; whereby the adjusted angle is maintained until readjusted. From the foregoing, it will be noted that the dentist can regularly adjust the angular relationship to suit a particular working condition. The known dental brushes do not permit such adaptation.

Figure 12:
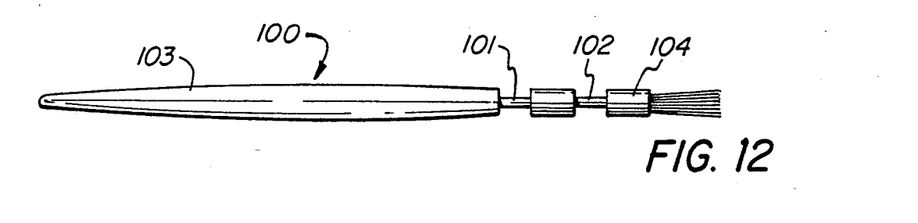
FIG. 12 illustrates a further modification illustrated as a straight brush.
Figure 13:
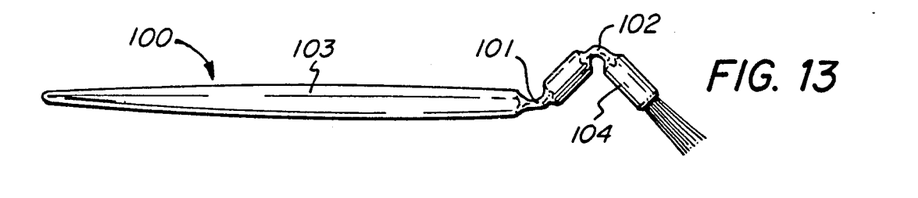
FIG. 13 illustrates the brush modification of FIG. 12 in its bent position.

FIGS. 12 and 13 illustrate still another form of the invention. The dental brush 100 of FIGS. 12 and 13 is similar to that described with respect to FIG. 1, except that brush 100 is provided with a plurality of bendable or flexible hinge sections 101 and 102, longitudinally spaced along the handle portion 103 adjacent the brush end 104. The construction of FIGS. 12 and 13 enables the dental brush to be bent at the two hinged sections 101 and 102 independently of each other to angularly dispose the brush end 104 at a compound angle relative to the longitudinal axis of the brush handle to provide the dentist with a greater degree of flexibility in reaching difficult or hard to reach areas. Such a compound bend is illustrated in FIG. 13. The multiple hinged portion provides for a "goose neck" type of adjustment for the brush end that will maintain the angularly disposed position of the brush. The rigidity and flexibility of the described constructions enables the brush to be used as a straight brush or as a multiple bend brush capable of access to the most difficult areas of the mouth, and which construction is suitable for making an economical brush that is sufficiently inexpensive so as to render it readily disposable after each use.

Figure 14:
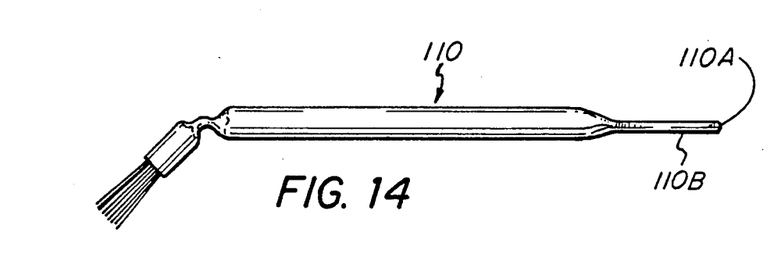
FIG. 14 is another brush modification.
Figure 15:
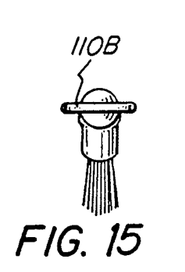
FIG. 15 is a detail end view of the brush of FIG. 14.

FIGS. 14 and 15 are directed to a further dental brush modification 110. Dental brush 110 differs from those previously described by providing at the free end 110A of the handle portion a flat end 110B to define a flat spatula end. Such spatula end can be utilized by the dentist to mix the ingredients of the material he desires to paint onto a patient's tooth. With the exception of the spatula end portion 110B, the dental brush proper may be formed in accordance to any of the described embodiments.

Figure 16:
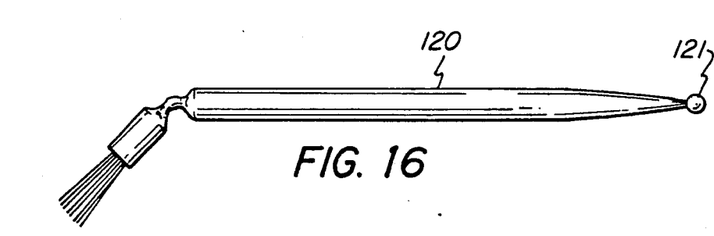
FIG. 16 is another brush modification.

FIG. 16 discloses a further modification, wherein the dental brush 120, which may be formed or constructed like any of the foregoing described modifications, is provided with a ball tip 121 at the free end of the handle portion, i.e., the end opposite the brush end. The ball tip 121 can be used as a packing ball by the dentist in those procedures requiring the dentist to pack or fill a tooth with dental material.

Figure 17:
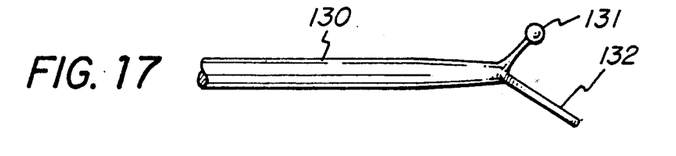
FIG. 17 is yet another brush modification embodying the invention.

FIG. 17 is a further modification of a dental brush wherein the free end of the brush handle 130 is provided with both a packing ball tip 131 as described in FIG. 14 and an angularly disposed flat spatula portion 132.

Figure 18:
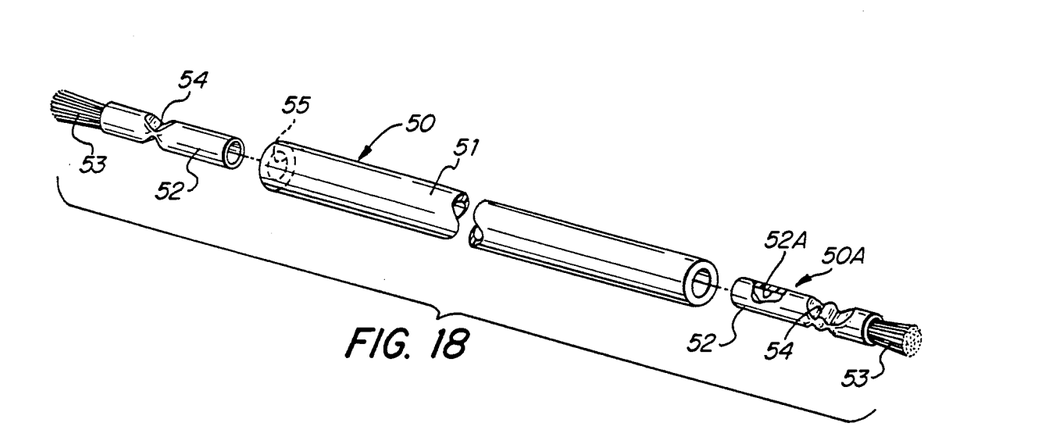
FIG. 18 is a perspective exploded view of another modification embodying the invention.
Figure 19:
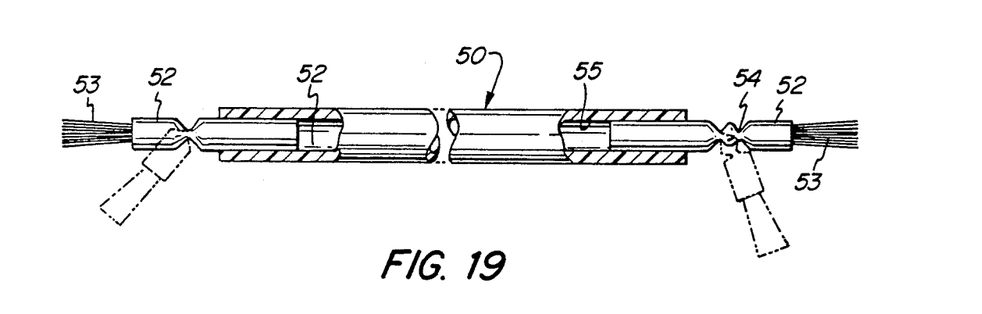
FIG. 19 is a side view of the dental brush of FIG. 18 in the assembled form and having parts shown in section.

FIGS. 18 and 19 are directed to another modified form of the invention. In this form, the handle portion 51 of the dental brush 50 comprises an elongated tubular member of any desired cross-section shape. The handle portion 51 of the illustrated embodiment is circular in cross-section and is provided with a bore 55 extending therethrough. In this embodiment, the brush end 50A comprises a relatively short tubular holder or sleeve 52 which has a bore 52A extending therethrough. A tuft of bristles 53 is secured in one end of the tubular brush holder 52; and which bristles are secure therein as hereinbefore described. Intermediate the ends of the short tubular brush holder 52 is a crimp or reduced portion 54 as hereinbefore described to provide a living hinge about which the brush 53 can be angularly disposed, as shown in the dotted position in FIG. 19.

It will be understood that the brush end 50A is detachably connected to the free end of the handle 50 by a frictional retention of the tubular brush holder 52 within the bore 55 of the brush handle portion 51. The short tubular brush holder 52 is preferably made of a resilient plastic material having a memory characteristic which permits the brush or bristles 53 to be maintained at an angle when bent about the hinge section 54; as shown in FIG. 19. With the construction described, it will be apparent that a brush end 52 may be attached to both ends of the handle portion 51. Thus, the dentist may use the construction of FIGS. 18 and 19 as a single ended dental brush or alternatively as a double end brush, which allows the dentist to use the same brush for working with and applying different materials to a patient's teeth. Upon completion of a given procedure, the brush and/or brush ends are rendered readily disposable.

Figure 20:
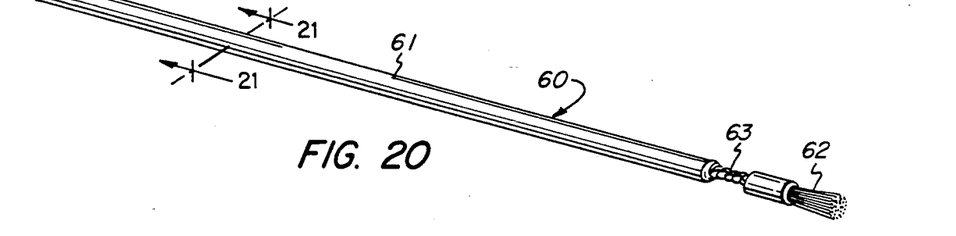
FIG. 20 is another modified embodiment.
Figure 21:
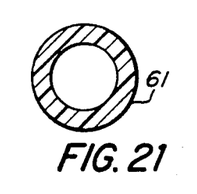
FIG. 21 is a section view taken on line 21—21 on FIG. 20.
Figure 22:
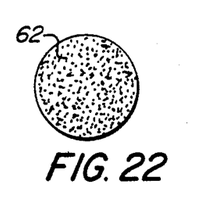
FIG. 22 is an end view of the brush end of FIG. 20.

FIGS. 20, 21 and 22 are directed to another form of the invention. In this form, the dental brush 60 comprises an elongated tubular handle 61 of any desired cross-sectional shape in which a tuft of bristles 62 are secured at one end of the handle 61 as hereinbefore described. In this form of the invention, the plastic elongated handle 61 is provided with a living hinge section 63, which is formed in the nature of a spiral or helix. The utilization of a spiral or helical hinge section as shown in FIG. 20 enables the brush end 62 to be angularly bent in any direction relative to the longitudinal axis of the handle portion, i.e. the brush end 62 can be bent at any angle within a range of 360 degrees relative to the axis of the handle, and the nature of the plastic being such that the angle is maintained in the set position.

Figure 24:
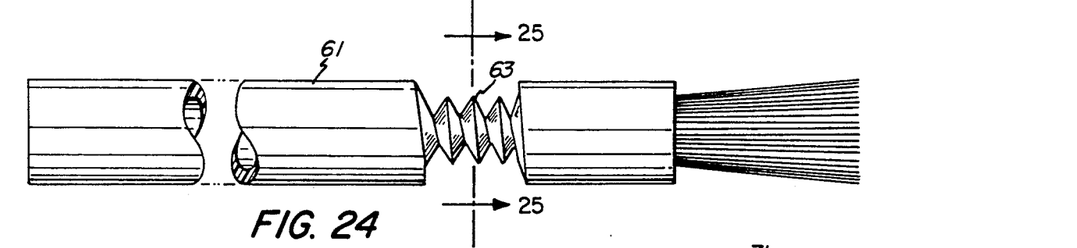
FIG. 24 is an enlarged side view of the embodiment of FIG. 20.

FIG. 24 illustrates a dental brush 70 similar to that described with respect to FIG. 20, except that the spiral or helical hinge section 71 is formed with its major diameter substantially equal to the outer diameter of the brush handle portion 72, whereby the bore 73 extends through the length of the brush handle 72 and the hinged spiral section 71.

Figure 25:
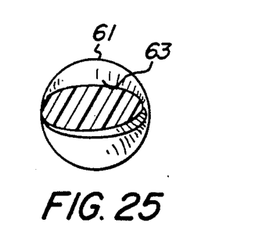
FIG. 25 is a section view taken along line 25—25 on FIG. 24.

FIG. 25 is an enlarged detail of the dental brush 60 described with respect to FIG. 20. As shown in the enlarged detail, the helical hinge section is formed on a reduced section either by molding or compression. As shown in FIG. 25, the cross-section of the helical hinge portion is solid, but flexible. In all other respects, the brush 61 functions as described with respect to FIGS. 20 and 23.

Figure 26:
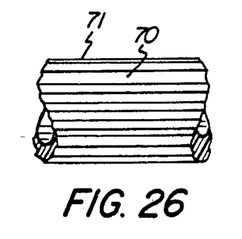
FIG. 26 is a fragmentary side view of a modified handle construction.
Figure 27:
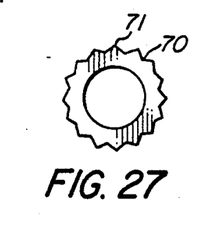
FIG. 27 is an end view of FIG. 26.

FIGS. 26 and 27 illustrate a modified form of handle construction. As shown, the handle portions of the dental brushes described may be provided with longitudinally extending grooves 70 and ridges 71 as shown, which facilitates the gripping of the brush by the users, particularly when the user may be wearing rubber gloves.

Figure 23:
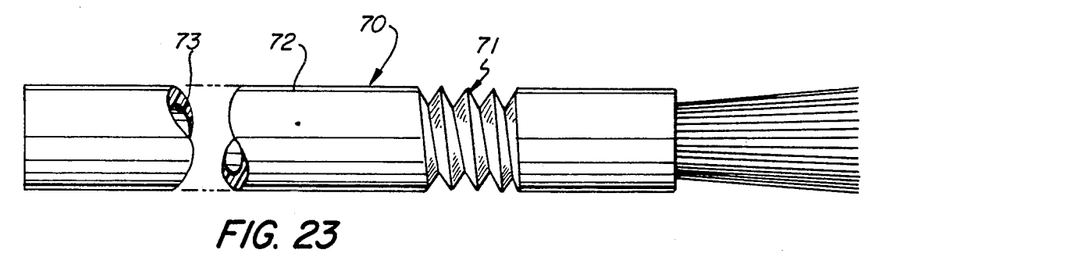
FIG. 23 is an enlarged view of a modified embodiment.

It will be understood that the tuft of bristles may be of equal length as shown in FIGS. 23 or 24, or the tufts can be shaped to define a chisel edge or knife edge or otherwise suitable shape as may be required to perform a selected procedure.

Figure 28:
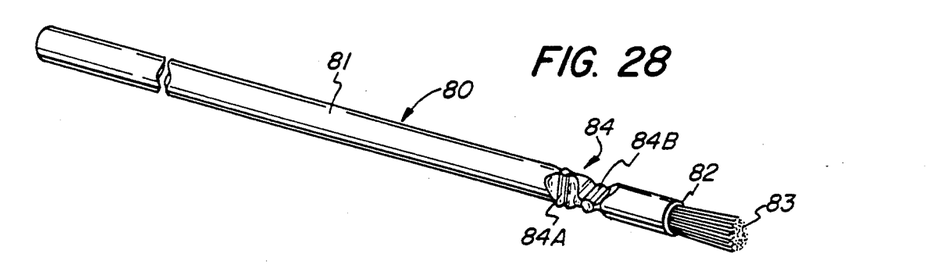
FIG. 28 is a perspective view of another modified embodiment.
Figure 29:
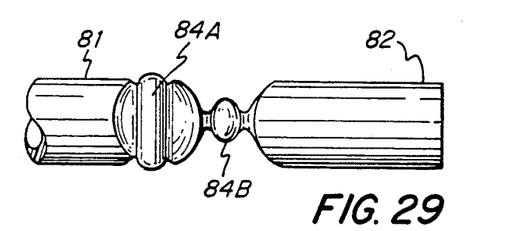
FIG. 29 is an enlarged detail of the hinge construction of the FIG. 28 embodiment.

FIGS. 28 and 29 illustrate another form of dental brush 80. In this form, the brush handle 81 comprises an elongated plastic member which is provided at one end with a seat or opening 82 in which a tuft of bristles 83 is secured in the manner herein described.

Adjacent the brush end 83, the handle portion is provided with a flexible hinge construction 84 which is formed of adjacent hinge sections 84A and 84B consisting of essentially flattened portions which are disposed in an out of phase relationship to define a universal type of joint connection which enables the brush end 83 to be bent at a compound angle relative to the axis of the brush handle 81. Thus, the brush end can be flexible between a 180 degree angle about hinge section 84B in a vertical direction and in a 180 degree arc in a lateral or horizontal direction as viewed in FIG. 28.

Figure 30:
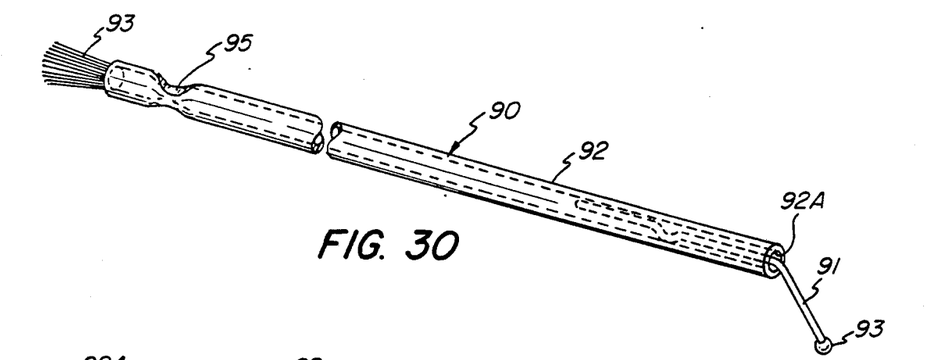
FIG. 30 is a perspective view of another modified embodiment.
Figure 31:
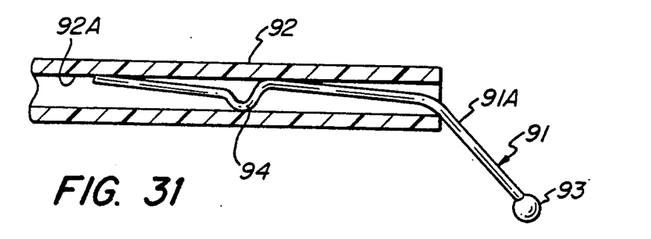
FIG. 31 is an enlarged detail of the embodiment shown in FIG. 30.

FIG. 30 and 31 illustrates another embodiment. The dental brush 90 of FIGS. 30 and 31 is similar in construction to that described with respect to FIG. 5, except that a burnishing tool 91 is detachably connected to the end of the handle portion 92 opposite the brush end 93. The burnishing tool 91 comprises a wire shank 91A which is provided with a ball burnisher 93 at the free end thereof. The other end of the shank 91A is received within the bore 92A of the handle portion 92. To frictionally retain the burnishing tool within the handle portion 92, an intermediate portion of the shank 91A is provided with a reverse bend 94 that engages the internal wall of the bore with the opposite ends of the bend 94 engage an opposed wall surface of the bore 92A to frictionally retain the burnishing tool in position within the bore 92A.

Adjacent the brush end 93, the handle is provided with a hinge section 95 similar to that of FIG. 5.

Figure 32:
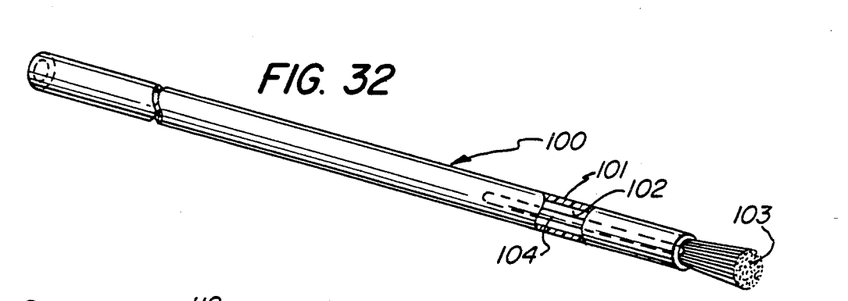
FIG. 32 is another modified embodiment.

FIG. 32 illustrates another dental brush construction. In this form, the dental brush 100 comprises an elongated flexible tubular member 101 which has a bore 102 therethrough. A tuft of brush bristles 103 are secured to one end of the handle 101. To provide flexibility to the brush end and to retain the brush end in an angularly disposed position, a wire length 104 is suitably connected to the internal surface of the bore; e.g. by adhesive or the like. Accordingly, the brush end 103 can be angularly bent relative to the central axis of the handle 101 by bending the handle along the wire length 104. It will be understood that the wire length is formed of a material that will retain the bent handle in the angled state. In this embodiment, the brush end can be bent within a range or arc of 360 degrees about the center axis of the handle.

Figures 33, 34:
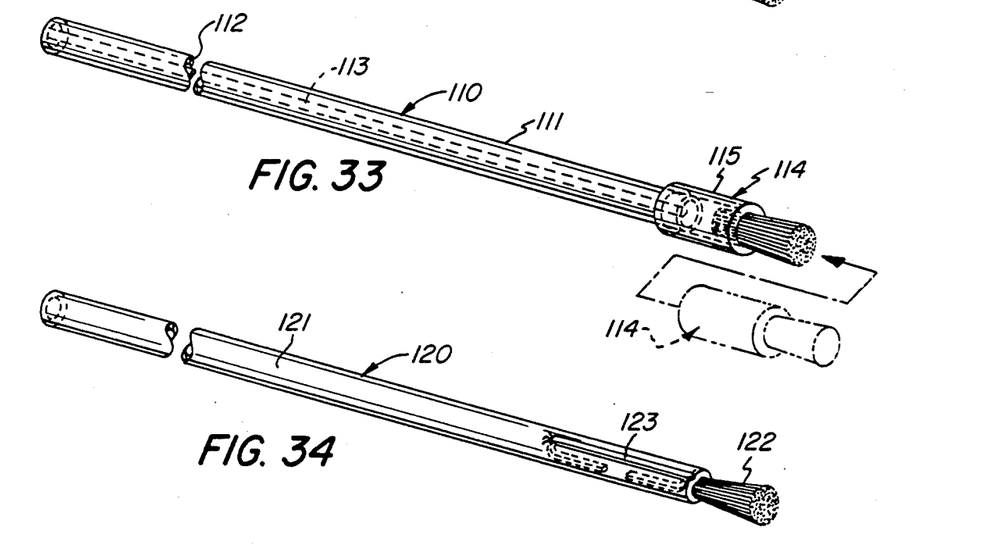
FIG. 33 is a perspective view of another embodiment.
FIG. 34 is an embodiment of yet another modification of the invention.

FIG. 33 illustrates another embodiment of the invention. In this form, the dental brush 110 comprises a tubular handle member 111 having a bore 112 extending therethrough. Connected to the internal surface of the bore 112 is a length of wire 113. The brush end 114 comprises a sleeve 115 in which a tuft of bristles 116 is connected in a manner as hereinbefore described. The other end of the brush sleeve 114 is frictionally attached to the end of the handle member 111 as shown. With this construction, the brush end 114 can be readily bent at an angle to the axis of the handle member anywhere along the length of wire 113. In this form of the invention, the disposable portion may be only the brush end or the entire brush end and handle member. This embodiment also has the advantage in that the brush end may be bent at any point along the handle of the brush as may be desired by the user.

FIG. 34 illustrates a further embodiment. In this embodiment, the dental brush 120 comprises an elongated tubular handle 121 in which the tuft of bristles 122 are folded about one end of a U-shaped staple 123 and which staple is then inserted into the bore of the handle 120.

From the foregoing, it will be apparent that the described dental brushes can be readily fabricated of low cost material so as to render it economically feasible to render them totally expendable after each use. The described dental brushes also eliminate completely the clean up and/or sterilizing problems heretofore encountered in a dental office with the prior known dental brushes. There are no brush tips to be cleaned or changed. Cross-contamination is eliminated, and most importantly is the fact that the described brushes permit a dentist to use the same either as a straight brush or a bent brush to achieve any desired contra-angle necessary to maximize access to even the most difficult to reach areas of the mouth.

While the invention has been described with respect to particular embodiments thereof, it will be understood that variations and modifications may be made without departing from the spirit or scope of the invention.

What is claimed is:

1. A readily disposable dental brush for applying various dental materials to a tooth in thin, even coatings comprising
   an elongated tubular handle member having a bore extending co-extensively therethrough,
   said handle member being open on at least one end,
   a relatively short tubular brush holder having an external diameter sized to be frictionally received within the bore of said handle member at said one end thereof,
   a tuft of bristles connected to one end of said brush holder,
   and means intermediate the ends of said brush holder defining a hinge section about which said bristles can be angularly disposed relative to the axis of said brush holder.

2. A readily disposable dental brush as defined in claim 11 and including a handle member open at the other end thereof,
   a second relatively short tubular brush holder having an external diameter sized to be frictionally received within said bore of said handle member at the other end thereof,
   a tuft of bristles connected to one end of said second brush holder,
   and means intermediate the ends of said second brush holder defining a hinge section about which the bristles of said second brush holder can be angularly disposed relative to the axis of said second brush holder.

3. A readily disposable dental brush for applying various dental materials to a tooth in thin even coatings comprising
   an elongated tubular handle member having a bore extending therethrough,
   a brush holder detachably connected to each end of said handle member,
   each of said brush holders comprising a relatively short tubular sleeve,
   a tuft of bristles connected to one end of said sleeve,
   said tubular sleeves having an external diameter sized to be frictionally received within the bore of said handle member,
   and a means defining a flexible hinge disposed intermediate each of said tubular sleeves,
   said latter means including a flattened reduced section forming the hinge about which the brush end of said sleeve is set in an angularly disposed position relative to the axis of said handle member.

4. A dental brush as defined in claim 3 wherein said brush holder is formed of a plastic material capable of being angularly flexed and retaining said angularly flexed position.

* * * * *